United States Patent
Shuros et al.

(10) Patent No.: US 8,855,772 B2
(45) Date of Patent: Oct. 7, 2014

(54) SYSTEM FOR NEURAL THERAPY

(75) Inventors: Allan C. Shuros, St. Paul, MN (US);
Craig Stolen, New Brighton, MN (US);
Timothy Meyer, North Oaks, MN (US);
Stephen Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1129 days.

(21) Appl. No.: 12/269,558

(22) Filed: Nov. 12, 2008

(65) Prior Publication Data

US 2009/0125076 A1    May 14, 2009

Related U.S. Application Data

(60) Provisional application No. 60/987,983, filed on Nov. 14, 2007.

(51) Int. Cl.
| | |
|---|---|
| *A61N 1/18* | (2006.01) |
| *A61N 1/32* | (2006.01) |
| *A61N 1/08* | (2006.01) |
| *A61N 1/36* | (2006.01) |

(52) U.S. Cl.
CPC ............. *A61N 1/08* (2013.01); *A61N 1/36114* (2013.01); *A61N 1/36071* (2013.01)
USPC ............................................... 607/45; 607/2

(58) Field of Classification Search
USPC .................................................. 607/3, 45, 2
See application file for complete search history.

(56) References Cited

U.S. PATENT DOCUMENTS

| | | |
|---|---|---|
| 2003/0040009 A1 | 2/2003 | Denny et al. |
| 2005/0209645 A1* | 9/2005 | Heruth et al. ................. 607/3 |
| 2005/0221348 A1* | 10/2005 | Ray et al. ...................... 435/6 |
| 2006/0241697 A1 | 10/2006 | Libbus et al. |
| 2007/0100378 A1* | 5/2007 | Maschino ..................... 607/2 |
| 2007/0179558 A1* | 8/2007 | Gliner et al. ................. 607/45 |
| 2008/0039895 A1* | 2/2008 | Fowler et al. ................. 607/2 |

FOREIGN PATENT DOCUMENTS

| | | |
|---|---|---|
| JP | 10510180 A | 10/1998 |
| JP | 2004533297 A | 11/2004 |
| WO | WO-9617546 A1 | 6/1996 |
| WO | WO-02096512 A1 | 12/2002 |
| WO | WO-2005/089860 A1 | 9/2005 |
| WO | WO-2007073455 A1 | 6/2007 |
| WO | WO-2007087192 A2 | 8/2007 |
| WO | WO-2007/121133 A2 | 10/2007 |

OTHER PUBLICATIONS

"International Application Serial No. PCT/US2008/012681, Written Opinion mailed Apr. 16, 2009", 9 pgs.
"International Application Serial No. PCT/US2008/012681, International Search Report mailed Apr. 16, 2009", 4 pgs.

(Continued)

*Primary Examiner* — Carl H Layno
*Assistant Examiner* — Jon Eric C Morales
(74) *Attorney, Agent, or Firm* — Schwegman Lundberg & Woessner, P.A.

(57) ABSTRACT

This document discusses, among other things, a system and method for calculating a neural stimulation energy at an external patient management (EPM) system using received information about a chemical characteristic indicative of a physiological state of a subject.

20 Claims, 4 Drawing Sheets

(56) References Cited

OTHER PUBLICATIONS

Boomsma, F., et al., "Plasma semicarbazide-sensitive amine oxidase (SSAO) is an independent prognostic marker for mortality in chronic heart failure.", *Eur Heart J.*, 21(22), (2000), 1859-1863

Boomsma, F., et al., "Plasma semicarbazide-sensitive amine oxidase is elevated in patients with congestive heart failure", *Cardiovasc Res.*, 33(2), (1997), 387-391.

Kurkijärvi, R., et al., "Circulating form of human vascular adhesion protein-1 (VAP-1): increased serum levels in inflammatory liver diseases.", *J Immunol.*, 161(3), (1998), 1549-1557.

Raine, A. E., et al., "Atrial natriuretic peptide and atrial pressure in patients with congestive heart failure", *N Engl J Med.*, 315(9):, (1986), 533-537.

Salmi, M., et al., "Insulin-regulated increase of soluble vascular adhesion protein-1 in diabetes", *Am J Pathol.*, 161(6), (2002), 2255-2262.

Wilson, E. M., et al., "Plasma matrix metalloproteinase and inhibitor profiles in patients with heart failure", *J Card Fail.*, 8(6), (2002), 390-398.

"Japanese Application Serial No. 2010-534024, Office Action mailed Mar. 27, 2012", With English Translation, 14 pgs.

"Japanese Application Serial No. 2010-534024, Response filed Jun. 27, 2012 to Office Action mailed", English claims with response, 9 pgs.

"Japanese Application Serial No. 2010-534024, Office Action mailed Nov. 6, 2012", 8 pgs.

"Japanese Application Serial No. 2010-534024, Response filed Jan. 31, 2013 to Office Action mailed Nov. 6, 2012", With English Claims, 10 pgs.

"European Application Serial No. 08850901.3, Examination Notification Art. 94(3) mailed Aug. 7, 2013", 7 pgs.

\* cited by examiner

SYSTEM FOR NEURAL THERAPY

CROSS-REFERENCE TO RELATED APPLICATION

This application claims the benefit of U.S. Provisional Application No. 60/987,983, filed on Nov. 14, 2007, under 35 U.S.C. §119(e), which is hereby incorporated by reference.

TECHNICAL FIELD

This patent document pertains generally to neural therapy, and more particularly, but not by way of limitation, to a system for neural therapy.

BACKGROUND

Neural stimulation has been proposed as a therapy for a number of physiological conditions. Examples of neural stimulation therapies include neural stimulation therapies for respiratory problems such a sleep disordered breathing, blood pressure control such as to treat hypertension, cardiac rhythm management, myocardial infarction and ischemia, heart failure, epilepsy, depression, pain, migraines, eating disorders and obesity, and movement disorders.

Overview

This overview is intended to provide an overview of the subject matter of the present patent application. It is not intended to provide an exclusive or exhaustive explanation of the invention. The detailed description is included to provide further information about the subject matter of the present patent application.

This document discusses, among other things, a system and method for calculating a neural stimulation energy at an external patient management (EPM) system using received information about a chemical characteristic indicative of a physiological state of a subject.

In Example 1, a system includes an external patient management (EPM) system configured to receive information about a chemical characteristic indicative of a physiological state of a subject and to calculate a neural stimulation energy using the received information.

In Example 2, the EPM system of Example 1 is optionally configured to modulate at least one neural stimulation parameter using the received information about the chemical characteristic.

In Example 3, the system of any one or more of Examples 1-2 optionally includes a chemical sensor, operatively communicatively coupled to the EPM system of any one or more of Examples 1-2, the chemical sensor configured to sense the chemical characteristic indicative of the physiological state of the subject.

In Example 4, the chemical sensor of any one or more of Examples 1-3 optionally includes an external chemical sensor.

In Example 5, the chemical sensor of any one or more of Examples 1-4 is optionally configured to sense at least one biomarker, the biomarker including a substance indicative of a physiological state of the subject.

In Example 6, the system of any one or more of Examples 1-5 optionally includes an implantable neural stimulator, operatively communicatively coupled to the EPM system of any one or more of Examples 1-5, the implantable neural stimulator configured to generate the calculated neural stimulation energy for delivery of neural stimulation to a neural target of the subject.

In Example 7, the implantable neural stimulator of any one or more of Examples 1-6 is optionally configured to deliver vagal stimulation and the EPM system of any one or more of Examples 1-6 optionally includes a controller configured to modulate at least one vagal stimulation parameter using the received information about the chemical characteristic.

In Example 8, the EPM system of any one or more of Examples 1-7 optionally includes a memory configured to trend information derived from the chemical characteristic over time and a controller configured to calculate the neural stimulation energy using the trended information to provide chronic neural stimulation therapy.

In Example 9, the EPM system of any one or more of Examples 1-8 is optionally configured to detect a physiological condition using the trend.

In Example 10, the system of any one or more of Examples 1-9 optionally includes an activity sensor, operatively communicatively coupled to the EPM system of any one or more of Examples 1-9, the activity sensor configured to sense an activity signal indicative of physical activity of the subject, and wherein the EPM system if any one or more of Examples 1-9 is optionally configured to receive the activity signal and to calculate the neural stimulation energy using the received information about the chemical characteristic and the received activity signal.

In Example 11, the system of any one or more of Examples 1-10 optionally includes a physiological sensor, operatively communicatively coupled to the EPM system of any one or more of Examples 1-10, the physiological sensor configured to sense a physiological parameter indicative of a physiological state of the subject, and wherein the EPM system of any one or more of Examples 1-10 is optionally configured to receive the physiological parameter and to calculate the neural stimulation energy using the received information about the chemical characteristic and the received physiological parameter.

In Example 12, the physiological sensor of any one or more of Examples 1-11 optionally includes a cardiac sensor configured to sense an intrinsic electrical cardiac signal as the physiological parameter.

In Example 13, a system includes a chemical sensor configured to sense a chemical characteristic indicative of a physiological state of a subject, an external patient management (EPM) system, operatively communicatively coupled to the chemical sensor, the EPM system configured to receive information about the sensed chemical characteristic and to calculate a neural stimulation energy using the received information, and an implantable neural stimulator, operatively communicatively coupled to the EPM system, the implantable neural stimulator configured to receive the calculated neural stimulation energy and to generate the calculated neural stimulation energy for delivery of neural stimulation to a neural target of the subject.

In Example 14, a method includes receiving, at an external patient management (EPM) system, information about a chemical characteristic indicative of a physiological state of a subject, calculating a neural stimulation energy at the EPM system using the received information about the chemical characteristic, and providing an indication of the calculated neural stimulation energy to a user or an automated process.

In Example 15, the calculating the neural stimulation energy of Example 14 optionally includes modulating at least one neural stimulation parameter using the received information about the chemical characteristic.

In Example 16, the method of any one or more of Examples 14-15 optionally includes sensing the chemical characteristic indicative of the physiological state of the subject.

In Example 17, the sensing the chemical characteristic of any one or more of Examples 14-16 optionally includes using an external chemical sensor.

In Example 18, the sensing the chemical characteristic of any one or more of Examples 14-17 optionally includes sensing at least one biomarker, the biomarker including a substance indicative of a physiological state of the subject.

In Example 19, the method of any one or more of Examples 14-18 optionally includes generating the neural stimulation energy for delivery of neural stimulation to a neural target of the subject.

In Example 20, the generating the neural stimulation energy of any one or more of Examples 14-19 optionally includes generating vagal stimulation energy and the calculating the neural stimulation energy of any one or more of Examples 14-19 optionally includes modulating at least one vagal stimulation parameter using the received information about the chemical characteristic.

In Example 21, the method of any one or more of Examples 14-20 optionally includes trending, at the EPM system of any one or more of Examples 14-20, information derived from the received information about the chemical characteristic over time, and the method of any one or more of Examples 14-20 optionally includes calculating the neural stimulation energy at the EPM system of any one or more of Examples 14-20 using the trended information to provide chronic neural stimulation therapy.

In Example 22, the method of any one or more of Examples 14-21 optionally includes detecting a physiological condition using the trended information.

In Example 23, the method of any one or more of Examples 14-22 optionally includes sensing an activity signal indicative of physical activity of the subject, receiving, at the EPM system of any one or more of Examples 14-22, information about the activity signal, and calculating the neural stimulation energy at the EPM system of any one or more of Examples 14-22 using the received information about the chemical characteristic and the received information about the activity signal.

In Example 24, the method of any one or more of Examples 14-23 optionally includes sensing a physiological parameter indicative of a physiological state of the subject, receiving, at the EPM system of any one or more of Examples 14-23, information about the physiological parameter, and calculating the neural stimulation energy at the EPM system of any one or more of Examples 14-23 using the received information about the chemical characteristic and the received information about the physiological parameter.

In Example 25, the sensing the physiological parameter of any one or more of Examples 14-24 optionally includes sensing an intrinsic electrical cardiac signal.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
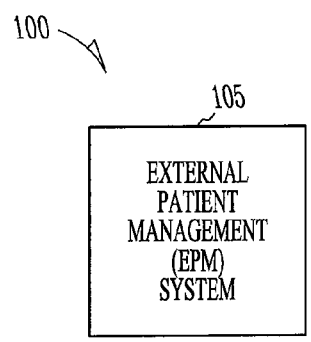
FIG. 1 illustrates generally an example of a system including a external patient management (EPM) system.

FIG. 1 illustrates generally an example of a system 100 including an external patient management (EPM) system 105. The EPM system 105 is located external to the subject and can be positioned local to the subject, e.g., within the immediate area of the subject, or can be positioned remote from the subject, e.g., outside of the immediate area of the subject. In various examples, the EPM system can be configured to manage a single subject, or the EPM can be configured to manage a population of subjects. In certain examples, the EPM system can include a memory, a controller, or other components.

In an example, the EPM system 105 can be configured to receive information about a chemical characteristic indicative of a physiological state of a subject, such as by using a receiver or one or more other data inputs, and to calculate a neural stimulation energy using the received information.

The received information about the chemical characteristic indicative of a physiological state of the subject can include information about a biomarker, an indicator of a biological state or a cellular status or condition. In certain examples, the biomarker can include at least one of matrix metalloproteinase (MMP), tissue inhibitor of metalloproteinases (TIMP), brain natriuretic peptide (BNP), atrial natriuretic peptide (ANP), C-reactive protein (CRP), vascular adhesion protein-1 (VAP-1), semicarbazide-sensitive amine oxidase (SSAO), protein kinase B (PKB), AKT, phospholamban, phosphorylated phospholamban, catecholamine, norephinepherine, cytokine, tumor necrosis factor-alpha (TNF-alpha), fas ligand, interleukin-10 (IL-10), neurotransmitter, acetylcholine, serotonin, neuropeptide-Y, substance P, metabolic marker, cardiac enzyme, or one or more other biomarkers indicative of a physiological or biological status or state.

In an example, the received information about the chemical characteristic indicative of a physiological state of the subject can include information about MMP. MMP (e.g., MMP-2, MMP-9, etc.) is a zinc-dependant endopeptidase, or a peptidase that breaks peptide bonds within the molecule, and can be capable of degrading extracellular matrix proteins or assisting in tissue or cardiac repair or remodeling. In an example, circulating plasma levels of MMP-2 and MMP-2 can be indicative of cardiomyopathy and can relate to the severity of the disease process. MMP can be inhibited by endogenous tissue inhibitor metalloproteinases (TIMP) (including TIMP-1, TIMP-2, TIMP-3 or TIMP-4).

In an example, the received information about the chemical characteristic indicative of a physiological state of the subject can include information about BNP. BNP is a 32 amino acid polypeptide secreted by the ventricles of the heart in response to excessive stretching of myocytes (heart muscle cells) in the ventricles. In an example, BNP can be indicative of heart failure and can be used as a prognosis indicator, as BNP levels can be higher in patients having worse outcomes.

In an example, the received information about the chemical characteristic indicative of a physiological state of the subject can include information about ANP. ANP, atrial natriuretic factor (ANF), or atriopeptin, is a polypeptide hormone involved in the homeostatic control of body water, sodium, and adiposity. ANP can be released by atrial myocytes (muscle cells in the atria of the heart) in response to high blood pressure. In an example, ANP can be indicative of increased blood pressure, including increased atrial pressure, an indicator of cardiac heart failure.

In an example, the received information about the chemical characteristic indicative of a physiological state of the subject can include information about CRP. CRP is an acute phase reactant produced by the liver that can be indicative of inflammation, e.g., the level of CRP rises as inflammation occurs within the body. In an example, CRP can be indicative of inflammation, increased blood pressure, and cardiac heart failure.

In an example, the received information about the chemical characteristic indicative of a physiological state of the subject can include information about VAP-1. VAP-1 is a protein that can be indicative of cardiac heart failure severity, and is closely associated with SSAO or SSAO activity. In an example, an increased level of circulating VAP-1, or increased SSAO activity, can be indicative of cardiac heart failure or the severity of cardiac heart failure.

In other examples, the received information can include some other chemical characteristic, chemical property, or chemical analysis of the subject.

The EPM system 105 can calculate a neural stimulation energy using the received information about the chemical characteristic indicative of the physiological state of the subject. Generally, using the EPM system 105 to calculate the neural stimulation energy allows for a more adaptable and capable medical device. The present inventors have recognized that the capabilities and processing power of implantable devices are limited due to the nature of developing and producing implantable devices. An implantable system, once implanted, can be difficult to adapt or change to incorporate new or different technologies. Moreover, implantable devices are restrained by their limited power capabilities. In contrast, the present inventors have recognized that an external system, such as the EPM system 105, is not burdened with these limitations. By calculating the neural stimulation energy at the EPM system 105, the storage and processing of the received information is not burdened with the limitations associated with implantable devices.

In an example, the EPM system 105 can calculate the neural stimulation energy using only information received from the subject. In other examples, the EPM system 105 can calculated the neural stimulation energy using information received from the subject in combination with at least one of clinical information, e.g., information received from studies or other known information, or with information received from a population, e.g., a population of subjects monitored by the EPM system 105.

In an example, the calculating the neural stimulation energy can include calculating an initial neural stimulation energy or adjusting or otherwise modulating a previously established neural stimulation energy. In an example, the received information can be input into a closed-loop feedback system to calculate, modulate, or titrate the neural stimulation energy. In an example, the EPM system 105 can be configured to initiate or adjust, e.g., increase, the neural stimulation energy if the received information about the chemical characteristic indicative of the physiological state of the subject shows that the subject's physiological state is worsening. In another example, the EPM system 105 can be configured to initiate or adjust, e.g., decrease or cease, the neural stimulation energy if the received information about the chemical characteristic indicative of the physiological state of the subject shows that the subject's physiological state is improving. In other examples, the EPM system 105 can be configured to modulate at least one neural stimulation parameter, such as a stimulation rate, a stimulation waveform, a stimulation mode, a stimulation site, etc, using the received information about the chemical characteristic indicative of the physiological state of the subject. In various examples, the EPM system 105 can be configured to calculate the neural stimulation energy in response to an acute or short-term change or indication of a specific reaction to the subject, in response to a chronic or long-term change or indication of a disease state of the subject, or some combination or permutation of the acute and chronic changes.

In an example, a physician or other user can communicate with, issue instructions to, or receive information from the EPM system 105, such as through a network or other data communication channel.

Figure 2:
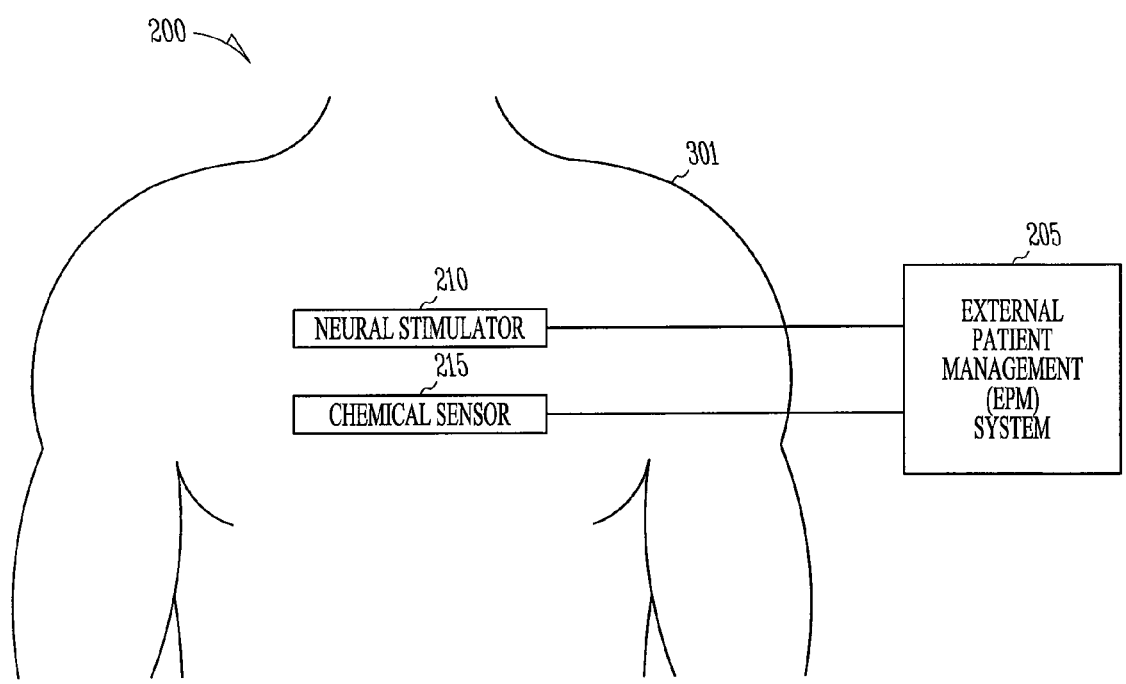
FIG. 2 illustrates generally an example of a system including an EPM system, a neural stimulator, and a chemical sensor.

FIG. 2 illustrates generally an example of a system 200 including a EPM system 205, a neural stimulator 210, and a chemical sensor 215.

In an example, the neural stimulator 210 can include an implantable neural stimulator. The neural stimulator 210 can be operatively communicatively coupled to the EPM system 205, such as via a wireless link or through a network. The neural stimulator 210 can be configured to generate the neural stimulation energy calculated at the EPM system 205, e.g., for delivery of neural stimulation to a neural target of the subject 201. In an example, the neural stimulator 210 can be configured to deliver vagal stimulation. In other examples, the neural stimulator 210 can be configured to deliver ganglion stimulation, spinal cord stimulation, baroreceptor stimulation, sympathetic stimulation, deep brain stimulation, or one or more other types of neural stimulation.

In certain examples, the chemical sensor 215 can include an implantable chemical sensor or an external chemical sensor, such as an external biological assay (bioassay) system. The bioassay system typically includes a system capable of measuring the quantitative or qualitative effect of a substance on a living organism. The chemical sensor 215 can be configured to sense a chemical characteristic indicative of the physiological state of the subject 201, such as at least one biomarker or other chemical characteristic, chemical property, or chemical analysis of the subject. In certain examples, the chemical sensor 215 can be configured to sense the chemical characteristic passively, such as by an implanted chemical sensor, or the chemical sensor 215 can be configured to sense the chemical characteristic actively, such as via a blood assay or one or more other bodily fluid assays.

In this example, the chemical sensor 215 can be operatively communicatively coupled to the EPM system 205, such as via a wireless link, through a network, or using another communication link. In other examples, the chemical sensor 215 can be coupled to the EPM system 205 directly, e.g., electrically or optically.

Figure 3:
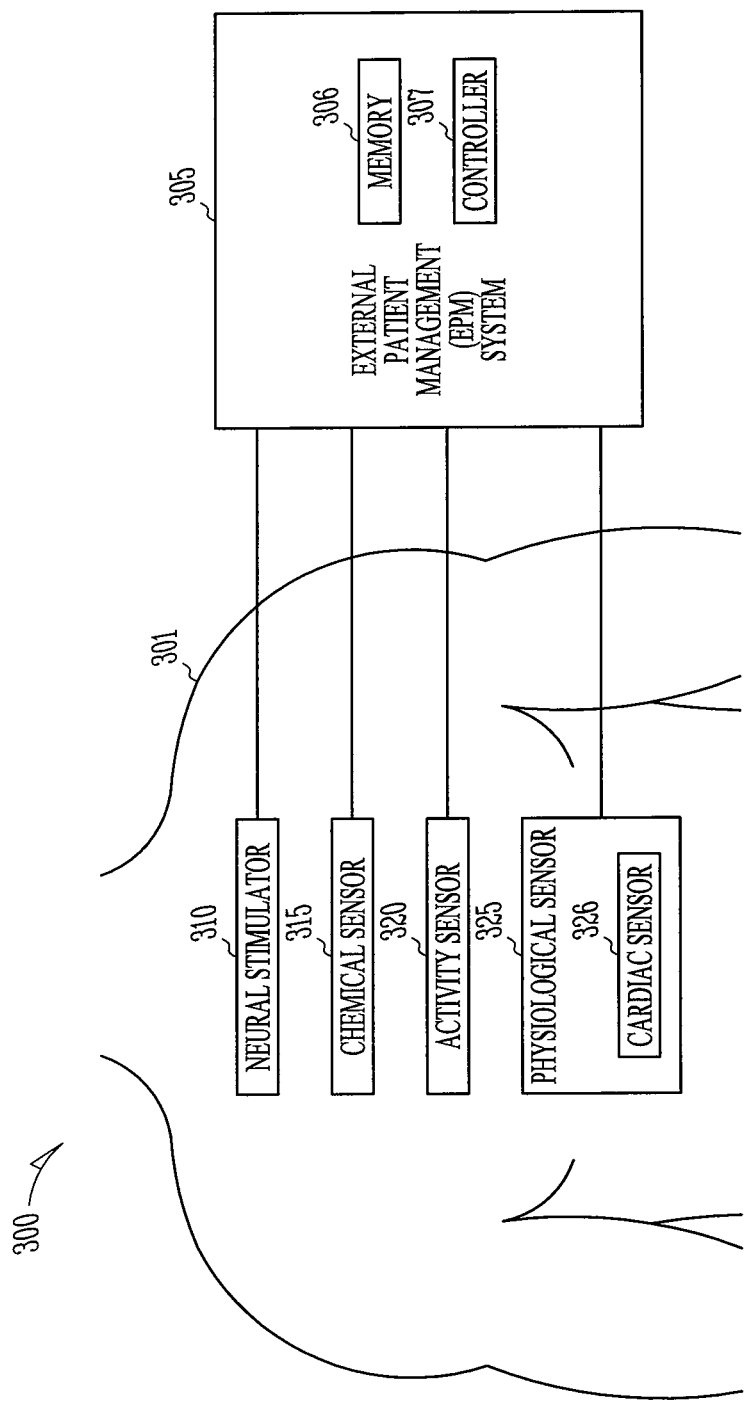
FIG. 3 illustrates generally an example of a system including an EPM system having a memory and a controller, a neural stimulator, a chemical sensor, an activity sensor, and a physiological sensor having a cardiac sensor.

FIG. 3 illustrates generally an example of a system 300 including a EPM system 305, a neural stimulator 310, and a chemical sensor 315.

In an example, the EPM system 305 can include a memory 306. The memory 306 can be configured to store and trend information derived from the information received over time about the chemical characteristic. The EPM system 305 can be configured to provide chronic long term monitoring or therapy using the trended information about the chemical characteristic.

In an example, the EPM system 305 can include a controller 307. The controller 307 can be configured to calculate the neural stimulation energy. In an example, the controller 307 can be configured to calculate the neural stimulation energy using the trended information about the chemical characteristic, e.g., in order to provide chronic neural stimulation therapy.

In an example, the EPM system 305 can be configured to detect a physiological condition, e.g., a specific disease state or physiological response, using the trended information. The EPM system 305 can be configured to store physiological information, such as the information about the chemical characteristic, on, about, or around specific known disease states, bodily responses, or physiological events. When the received information about the chemical characteristic, or other physiological information, is similar to that of the stored physiological information, such that it is likely that the disease state, bodily response, or physiological event has happened or will happen at some time, the EPM system 305 can calculate a neural stimulation energy in order to prevent or otherwise treat the predicted disease state, bodily response, or physiological event. Further, the EPM system 305 can communicate the calculated neural stimulation energy to the neural stimulator 310 in order to provide the calculated therapy. In other examples, the EPM system 305 can be configured to communicate other information, such as programming information or other instructions, to the neural stimulator 310 or other implantable devices. In an example, a physician or other use can communicate instructions to the EPM system 305, which can communicate the instructions to the neural stimulator 310 or other implantable device. In other examples, the neural stimulator 310 or other implantable device can be configured to send information to the EPM system 305, which can be configured to communicate with or send alerts to a user or physician.

In an example, the system 300 can include an activity sensor 320. The activity sensor 320 can be communicatively coupled to the EPM system 305, such as via a wireless link or through a network, and can be configured to sense an activity signal indicative of physical activity of the subject 301, such as the amount of subject's present motion or rest. The activity sensor 320 can be an implantable component, an external component, or a combination or permutation of an implantable component and an external component. In certain examples, the activity sensor 301 can include any device configured to sense the activity of the subject 301, such as an accelerometer, an impedance sensor, or other physiological sensor capable of sensing activity. In an example, the EPM system 305 can be configured to receive the activity signal and to calculate the neural stimulation energy using the received information about the chemical characteristic and the received activity signal.

In an example, the system 300 can include a physiological sensor 325. The physiological sensor 325 can be communicatively coupled to the EPM system 305, such as via a wireless link or through a network, and can be configured to sense a physiological parameter indicative of a physiological state of the subject. The physiological sensor 325 can be an implantable component, an external component, or a combination or permutation of an implantable component and an external component. In an example, the EPM system 305 can be configured to receive the physiological parameter and to calculate the neural stimulation energy using the received information about the chemical characteristic and the received physiological parameter.

In an example, the physiological sensor 325 can include a cardiac sensor 326 configured to sense an intrinsic electrical cardiac signal of the subject 301 as the physiological parameter. The cardiac signal can include any signal indicative of the electrical or mechanical cardiac activity of the heart of the subject 301, e.g., an electrocardiogram (ECG) signal, an impedance signal, an acceleration signal, etc. In certain examples, the cardiac sensor 326 can include an intrinsic cardiac signal sensor, such as one or more than one electrode or lead to sense one or more than one depolarization, or the cardiac sensor 326 can include a mechanical sensor, such as an impedance sensor or an accelerometer to sense one or more than one contraction.

In other examples, the physiological sensor 325 can include other sensors, such as a posture sensor configured to sense a posture signal of the subject 301, a respiration sensor configured to sense the respiration of the subject 301, a neural activity sensor configured to sense the neural activity of the subject 301, a heart sound sensor configured to sense a heart sound signal of the subject 301, or one or more other physiological sensors.

In certain examples, the memory 306 of the EPM system 305 can be configured to store and trend information derived from the information received over time from the activity sensor 320 or the physiological sensor 325. In various examples, the EPM system 305 can be configured to provide chronic long term monitoring or therapy using the trended information from the activity sensor 320, the trended information from the physiological sensor 325, or a combination or permutation of the trended information from the activity sensor 320 and the physiological sensor 325. In other examples, the EPM system 305 can be configured to provide chronic long term monitoring or therapy using the trended information received from at least one of the activity sensor 320 or the physiological sensor 325 in conjunction with the trended information about the chemical characteristic.

In various examples, the controller 307 of the EPM system 305 can be configured to calculate the neural stimulation energy using the trended information from the activity sensor 320, the trended information from the physiological sensor 325, or a combination or permutation of the trended information from the activity sensor 320 and the physiological sensor 325. In other examples, the controller 307 can be configured to calculate the neural stimulation energy using the trended information from at least one of the activity sensor 320 or the physiological sensor 235 in conjunction with the trended information about the chemical characteristic.

Figure 4:
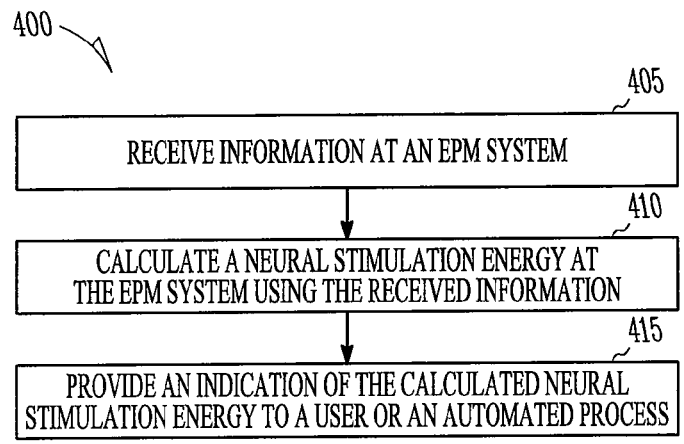
FIG. 4 illustrates generally an example of a method including receiving information at an EPM system and calculating a neural stimulation energy at the EPM system using the received information.

FIG. 4 illustrates generally an example of a method 400 including receiving information at an EPM system and calculating a neural stimulation energy at the EPM system using the received information.

At 405, information is received at an EPM system. The information can include information about a chemical characteristic indicative of a physiological state of a subject. In an example, the information can be received using a receiver or other data input of the EPM system, such as the EPM system 105.

At 410, a neural stimulation energy is calculated at the EPM system using the received information. The neural stimulation energy can include any stimulation energy adapted to provide neural stimulation therapy. The calculating the neural stimulation energy can include initializing, modulating, or otherwise calculating a neural stimulation energy in response to the received information. In an example, the neural stimulation energy is calculated using a closed-loop feedback system that takes into account the received information, e.g., information about the chemical characteristic indicative of a physiological state of the subject. Calculating the neural stimulation energy can include titrating or altering a current neural stimulation energy or therapy, modulating a neural stimulation parameter, or otherwise initiating or changing a neural stimulation energy configured to be delivered to a neural target of the subject. The calculating the neural stimulation energy can occur at the EPM system, such as the EPM system 105.

At 415, an indication of the calculated neural stimulation energy is provided to a user or an automated process. In an example, the providing the indication can include transmitting the calculated neural stimulation energy to a medical device, such as the neural stimulator 210 or other device capable of generating, delivering, or otherwise using the calculated neural stimulation energy, for use in an automated process, such as generating, delivering, or otherwise using the calculated neural stimulation energy. In other examples, the providing the indication of the calculated neural stimulation energy can include providing a warning or an alert to a physician or other user, such as by sending an electronic communication to the user including information about the calculated neural stimulation energy or some other information from the EPM system, e.g., information about the sensed chemical characteristic, etc.

Figure 5:
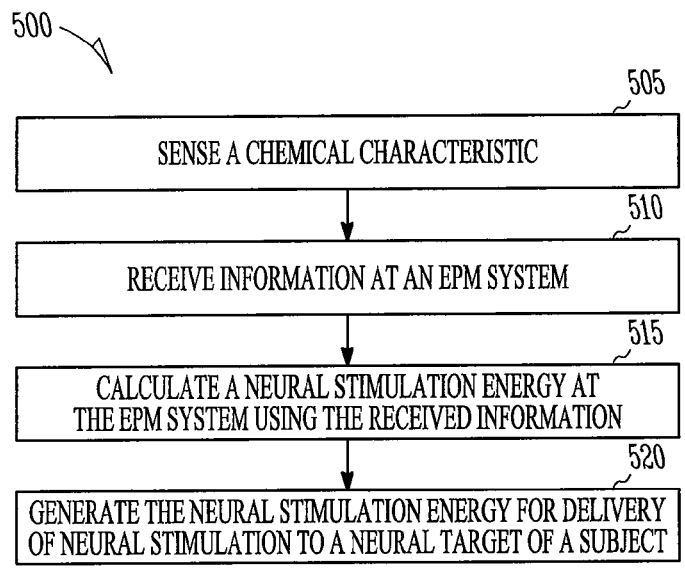
FIG. 5 illustrates generally an example of a method including calculating a neural stimulation energy at an EPM system using information about a sensed chemical characteristic.

FIG. 5 illustrates generally an example of a method 500 including calculating a neural stimulation energy at an EPM system using information about a sensed chemical characteristic.

At 505, a chemical characteristic is sensed. The chemical characteristic can include any chemical characteristic indicative of a physiological state of a subject. In an example, the chemical characteristic can include a biomarker, such as a protein, amino acid, neurotransmitter, or other chemical characteristic indicative of the physiological state, the biological state, or cellular status or condition of the subject. In certain examples, the chemical characteristic can be sensed using an external or implanted chemical sensor, such as the chemical sensor 215.

At 510, information is received at an EPM system. The information can include information from the sensed chemical characteristic. In an example, the information can be received, e.g., wirelessly received, at the EPM system, e.g., the EPM system 105, using a data input or one or more other communication links.

At 515, a neural stimulation energy is calculated at the EPM system using the received information. The neural stimulation energy can include any stimulation energy adapted to provide neural stimulation therapy. In an example, the EPM system can transmit the calculated neural stimulation energy to an implanted device for generation of the calculated neural stimulation energy.

In an example, if the received information is indicative of depression, e.g., if the received information shows that the serotonin, TNF-alpha, fas ligand, or IL-10 levels are outside a normal range, then a neurostimulation energy can be calculated to treat the detected depression, e.g., vagal stimulation.

In another example, if the received information is indicative of heart failure, e.g., if the received information shows that BNP, MMP, acetylcholine, norepinephrine, cytokine, or cardiac enzyme levels are outside a normal range, then a neurostimulation energy can be calculated to treat the detected treat heart failure.

The MMP-9 level in a healthy subject is typically 25±6 ng/mL. In an example, if the received information shows that the MMP-2 or MMP-9 level is above a threshold level, such as above MMP-9>60 ng/mL, then neurostimulation energy can be calculated to treat heart failure. In another example, neurostimulation parameters can be titrated based on changes in MMP levels. For example, if MMP-9 levels are falling, a current therapy can be maintained. If MMP-9 levels are constant or increasing, adjustments to a current therapy can be made, e.g., smaller adjustments for a constant MMP-9 level or larger adjustments for an increasing MMP-9 level.

Changes in the ratio of MMP and TIMP levels can be indicative of the progression or acceleration of the LV remodeling process in cardiac heart failure. In certain examples, a decrease in the ratio of MMP-2 and TIMP-1 or a decrease in the ratio of MMP-8 and TIMP-1 can be indicative of cardiac heart failure. In other examples, an increase in the ratio of MMP-9 and TIMP-1 or an increase in the ration of MMP-9 and TIMP-2 can be indicative of cardiac heart failure. Thus, in an example, if the received information shows that the ratio of MMP and TIMP levels has changed such that the change is indicative of heart failure, then a neurostimulation energy can be calculated to treat the detected heart failure.

The BNP level in a healthy subject is typically less than 100 pg/mL. In certain examples, a BNP level of 500 pg/mL or under can be required for hospital discharge, or a BNP level of 700 pg/mL can be indicative of decompensated congested heart failure. Thus, in an example, if the received information shows that the BNP level is above a threshold level, e.g., 500 pg/mL or 700 pg/mL, then neurostimulation energy can be calculated to treat the detected condition.

The ANP level in a healthy subject is typically less than 20 pmol per liter (e.g., 17±2 pmol per liter). An increased level of ANP (e.g., greater than 20 pmol per liter, such as 48±14 pmol per liter) can be indicative of elevated atrial pressure, an indicator of cardiac heart failure. Thus, in an example, if the received information shows that the ANP level is above a threshold level, e.g., 34 pmol per liter, 30 pmol per liter, 20 pmol per liter, etc., then neurostimulation energy can be calculated to treat the detected condition.

The circulating VAP-1 level in a healthy subject is typically 49 to 244 ng/mL. The circulating SSAO levels in a healthy subject is typically 150-550 mU/L. SSAO activity is expressed as the ability to produce pmol of bensaldehyde per mL of plasma per minute (mU/L). In an example, if the received information shows that the circulating VAP-1 level or the circulating SSAO level is above a threshold level (e.g., 244 ng/mL for the circulating VAP-1 level or 550 mU/L for the circulating SSAO level), then neurostimulation energy can be calculated to treat the detected condition. In other examples, as an increase in circulating SSAO activity is associated with diabetes, a different threshold level could be applied when there is a history of diabetes or high blood glucose measurements in the subject. Similar increases in circulating VAP-1 can also be used to adjust therapy. Because the diurnal and monthly intra-individual variations in the VAP-1 level is low (<25% and <20%) a change in >25% in the absence of reported or detected diabetes could be used as a threshold level for neurostimulation treatment of heart failure.

In other examples, if the received information is indicative of a physiological state of the subject that can be treated using neural stimulation, then a neurostimulation energy can be calculated to treat the sensed physiological state of the subject.

At 520, the neural stimulation energy is generated for delivery of neural stimulation to a neural target of a subject. In an example, the neural stimulation energy calculated at the EPM system can be received and generated using an implantable neural stimulator, such as the neural stimulator 210 or other implantable medical device capable of generating a neural stimulation energy. The generated neural stimulation energy can then be delivered to a neural target of the subject, such as the vagus nerve, specific areas of the brain, or one or more other neural targets to provide neural stimulation therapy.

Figure 6:
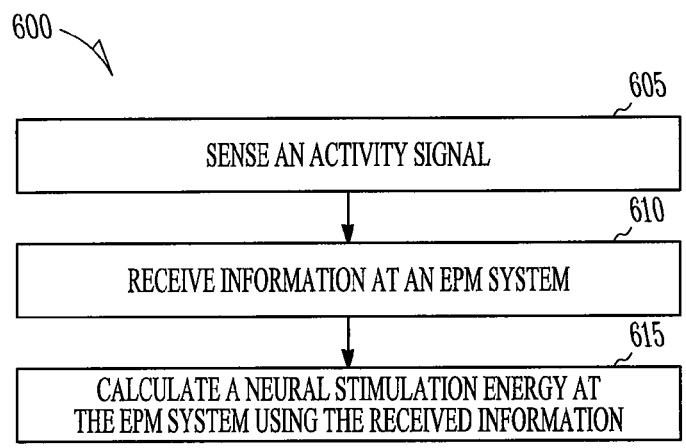
FIG. 6 illustrates generally an example of a method including calculating a neural stimulation energy at an EPM system using information about a sensed activity signal.

FIG. 6 illustrates generally an example of a method 600 including calculating a neural stimulation energy at an EPM system using information about a sensed activity signal.

At 605, an activity signal is sensed. The activity signal can include any signal indicative of the physical activity, motion, or rest of the subject. In an example, the activity signal can be sensed using an activity sensor, such as the activity sensor 320.

At 610, information is received at an EPM system. The information can include information from the sensed activity signal. In an example, the information can be received, e.g., wirelessly received, at the EPM system, e.g., the EPM system 105, using a data input or one or more other communication links.

At 615, a neural stimulation energy is calculated at the EPM system using the received information. The neural stimulation energy can include any stimulation energy adapted to provide neural stimulation therapy. In certain examples, the neural stimulation energy can be calculated using the information received from the sensed activity signal, the information received about the chemical characteristic, or a combination or permutation of the information received from the sensed activity signal and the information received about the chemical characteristic. In an example, the information from the sensed activity signal can be indicative of pain or depression, e.g., an acute or chronic lack of activity, increase in resting time, a violent increase in activity, such as during a fall or other accident, etc. This information can be used in conjunction with the information about the chemical characteristic to calculate a neurostimulation energy to treat the detected condition.

Figure 7:
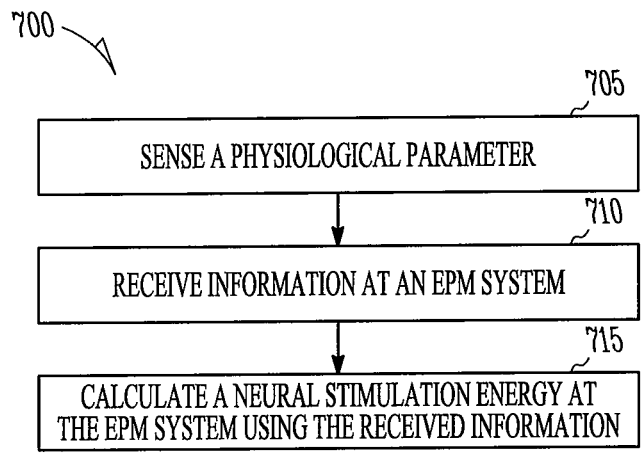
FIG. 7 illustrates generally an example of a method including calculating a neural stimulation energy at an EPM system using information about a sensed physiological parameter.

FIG. 7 illustrates generally an example of a method 700 including calculating a neural stimulation energy at an EPM system using information about a sensed physiological parameter.

At 705, a physiological parameter is sensed. The physiological parameter can include any parameter indicative of the physiological state of a subject, such as a cardiac signal, an impedance signal, a respiration signal, a posture signal, a neural activity signal, a heart sound signal, or one or more other physiological parameters. In an example, the physiological parameter can be sensed using the physiological sensor 325.

At 710, information is received at an EPM system. The information can include information from the sensed physiological parameter. In an example, the information can be received, e.g., wirelessly received, at the EPM system, e.g., the EPM system 105, using a data input or one or more other communication links.

At 715, a neural stimulation energy is calculated at the EPM system using the received information. The neural stimulation energy can include any stimulation energy adapted to provide neural stimulation therapy. In certain examples, the neural stimulation energy can be calculated using the information received from the sensed physiological parameter, the information received about the chemical characteristic, or a combination or permutation of the information received from the sensed physiological parameter and the information received about the chemical characteristic. In an example, the information from the sensed physiological parameter can be indicative of pain or depression, e.g., an acute or chronic increase or decrease in respiration, cardiac activity, the subject's weight, the subject's sleep pattern, etc. This information can be used in conjunction with the information about the chemical characteristic to calculate a neurostimulation energy to treat the detected condition.

In an example, the neural stimulation energy can be calculated using a combination or permutation of at least one of the information from the sensed chemical characteristic, the information from the sensed activity signal, or the information from the sensed physiological parameter.

Figure 8:
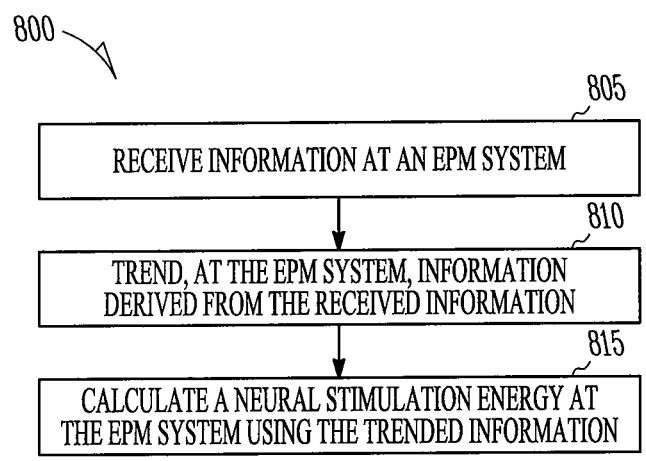
FIG. 8 illustrates generally an example of a method including calculating a neural stimulation energy at an EPM system using trended information.

FIG. 8 illustrates generally an example of a method 800 including calculating a neural stimulation energy at an EPM system using trended information.

At 805, information is received at an EPM system. The information can include at least one of information from the sensed chemical characteristic, information from the sensed activity signal, or information from the sensed physiological parameter. In an example, the information can be received, e.g., wirelessly received, at the EPM system, e.g., the EPM system 105, using a data input or one or more other communication links.

At 810, information derived from the received information is trended at the EPM system. In an example, the information, once received at the EPM system, can be stored in a memory, such as the memory 306. Once the information is received or stored in the memory, the EPM system can process the information, e.g., filter or otherwise manipulate the information to achieve useful data. In an example, the information can be processed using the controller 307. In an example, the information derived from the received information can include the processed information, which is then trended. Generally, a trend can include an index of information. In an example, at 810, the trended information can include an index of the processed information.

At 815, a neural stimulation energy is calculated at the EPM system using the trended information. In an example, if the trended information shows an acute change in the physiological state of the subject, then the EPM system can initiate, modulate, or otherwise calculate a neural stimulation energy to account for the acute change. In other examples, if the trended information shows a chronic change, or if the trended information appears similar to a known physiological state, e.g., clinically known, or a learned physiological state, e.g., learned from previous chemical, activity, or physiological information from the subject, then the EPM system can initiate, modulate, or otherwise calculate a neural stimulation energy to account for the chronic change or similar physiological state.

In an example, if the information from the sensed chemical characteristic indicates that the physiological state of the subject is worsening, e.g., if the CRP levels increase, then the EPM system can trend the received information and compare the trend to at least one of an absolute or relative change from the last sample or a larger collection of accumulated data, e.g., a rolling average or one or more other index of accumulated data. Once the trend has been compared, the neurostimulation energy can be calculated using the results of the comparison. Generally, different neurostimulation patterns elicit different therapeutic effects. In this example, CRP level increase is indicative of inflammation. Thus, the neurostimulation energy can be calculated to attenuate inflammation. In other examples, if the information from the sensed chemical characteristic or other physiological data, e.g., information about the sensed activity signal or the sensed physiological parameter, indicates an increase in cardiac metabolic demand, then the neurostimulation energy can be calculated to decrease HR, such as by delivering vagal stimulation.

In an example, a physiological condition can be detected using the trended information. If the trended information is similar to stored information, e.g., if the information from the sensed chemical characteristic or other physiological data appears similar to stored information from or prior to a known or learned physiological state, such as heart failure decompensation, an arrhythmia, etc., then an alert can be sent to a physician and therapy can be delivered to the subject in accordance therewith.

In the examples of FIG. 1-8, various examples, including receiving information about a chemical characteristic indicative of a physiological state of a subject, calculating a neural stimulation energy at an EPM system using the received information about the chemical characteristic, sensing the chemical characteristic indicative of the physiological state of the subject, generating the neural stimulation energy, trending information derived from the received information about the chemical characteristic over time, detecting a physiological condition using the trended information, sensing an activity signal indicative of physical activity of the subject, sensing a physiological parameter indicative of the physiological state of the subject, calculating the neural stimulation energy using received information about the activity signal, and calculating the neural stimulation energy using received information about the physiological parameter are disclosed. It is to be understood that the disclosed examples are not exclusive, and can be implemented either alone or in combination, or in various permutations or combinations.

Generally, the system or method disclosed herein can be described as a closed loop system for neural therapy. In certain examples, the neurostimulation energy delivered to the subject can affect the chemical characteristic sensed by the chemical sensor, which in turn can affect the calculation of the next neurostimulation energy to be delivered to the subject.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A system, comprising:
an external patient management (EPM) system configured to receive information about a chemical characteristic indicative of a physiological state of a subject, the EPM system including a memory and a control, the controller configured to provide trend information derived from the chemical characteristic received over time using the memory and to calculate a neural stimulation energy using the trend information, wherein the chemical characteristic includes at least one of matrix metalloproteinase, tissue inhibitor of metalloproteinases, brain natriaretic peptide, atrial natriaretic peptide, C-reactive protein, vascular adhesion protein, semicarbazide-sensitive amine oxidase, protein kinase B, AKT, phospholamban, phosphorylated phospholamban, catecholamine, norephinepherine, cytokine, tumor necrosis factor-alpha, fas ligand, interleukin, neurotransmitter, acetylcholine, serotonin, or neuropeptide-Y.

2. The system of claim 1, wherein the EPM system is configured to modulate at least one neural stimulation parameter using the received information about the chemical characteristic.

3. The system of claim 1, including a chemical sensor, operatively communicatively coupled to the EPM system, the chemical sensor configured to sense the chemical characteristic indicative of the physiological state of the subject.

4. The system of claim 3, wherein the chemical sensor includes an external chemical sensor.

5. The system of claim 1, including an implantable neural stimulator, operatively communicatively coupled to the EPM system, the implantable neural stimulator configured to generate the calculated neural stimulation energy for delivery of neural stimulation to a neural target of the subject.

6. The system of claim 5, wherein the implantable neural stimulator is configured to deliver vagal stimulation and the EPM system includes a controller configured to modulate at least one vagal stimulation parameter using the received information about the chemical characteristic.

7. The system of claim 1, wherein the EPM system is configured to detect a physiological condition using the trend information.

8. The system of claim 1, including an activity sensor, operatively communicatively coupled to the EPM system, the activity sensor configured to sense an activity signal indicative of physical activity of the subject; and
  wherein the EPM system is configured to receive the activity signal and to calculate the neural stimulation energy using the received information about the chemical characteristic and the received activity signal.

9. The system of claim 1, including a physiological sensor, operatively communicatively coupled to the EPM system, the physiological sensor configured to sense a physiological parameter indicative of a physiological state of the subject; and
  wherein the EPM system is configured to receive the physiological parameter and to calculate the neural stimulation energy using the received information about the chemical characteristic and the received physiological parameter.

10. The system of claim 9, wherein the physiological sensor includes a cardiac sensor configured to sense an intrinsic electrical cardiac signal as the physiological parameter.

11. A method, comprising:
  receiving, at an external patient management (EPM) system, information about a chemical characteristic indicative of a physiological state of a subject, wherein the chemical characteristic includes at least one of matrix metalloproteinase, tissue inhibitor of metalloproteinases, brain natriaretic peptide, atrial natriaretic peptide, C-reactive protein, vascular adhesion protein, semicarbazide-sensitive amine oxidase, protein kinase B, AKT, phospholamban, phosphorylated phospholamban, catecholamine, norephinepherine, cytokine, tumor necrosis factor-alpha, fas interleukin, neurotransmitter, acetylcholine, serotonin, or neuropeptide-Y;
  trending information derived from the received information about the chemical characteristic over time using a controller and memory of the EPM system to provide trended information;
  calculating a neural stimulation energy at the EPM system using the trended information about the chemical characteristic; and
  providing an indication of the calculated neural stimulation energy to a user or an automated process.

12. The method of claim 11, wherein the calculating the neural stimulation energy includes modulating at least one neural stimulation parameter using the received information about the chemical characteristic.

13. The method of claim 11, including sensing the chemical characteristic indicative of the physiological state of the subject.

14. The method of claim 13, wherein the sensing the chemical characteristic includes using an external chemical sensor.

15. The method of claim 11, including generating the neural stimulation energy for delivery of neural stimulation to a neural target of the subject.

16. The method of claim 15, wherein the generating the neural stimulation energy includes generating vagal stimulation energy and the calculating the neural stimulation energy includes modulating at least one vagal stimulation parameter using the received information about the chemical characteristic.

17. The method of claim 11, including detecting a physiological condition using the trended information.

18. The method of claim 1, including:
  sensing an activity signal indicative of physical activity of the subject;
  receiving, at the EPM system, information about the activity signal; and
  calculating the neural stimulation energy at the EPM system using the received information about the chemical characteristic and the received information about the activity signal.

19. The method of claim 11, including:
  sensing a physiological parameter indicative of a physiological state of the subject;
  receiving, at the EPM system, information about the physiological parameter; and
  calculating the neural stimulation energy at the EPM system using the received information about the chemical characteristic and the received information about the physiological parameter.

20. The method of claim 19, wherein the sensing the physiological parameter includes sensing an intrinsic electrical cardiac signal.

* * * * *